US008992690B1

(12) United States Patent
Kandemir (10) Patent No.: US 8,992,690 B1
(45) Date of Patent: Mar. 31, 2015

(54) FLAT BELT TREADMILL-LIKE ROTATION TOOTHBRUSH

(71) Applicant: Alexander Kandemir, New York, NY (US)

(72) Inventor: Alexander Kandemir, New York, NY (US)

( * ) Notice: Subject to any disclaimer, the term of this patent is extended or adjusted under 35 U.S.C. 154(b) by 72 days.

(21) Appl. No.: 14/029,864

(22) Filed: Sep. 18, 2013

(51) Int. Cl.
| | |
|---|---|
| *B08B 7/00* | (2006.01) |
| *A61C 17/34* | (2006.01) |
| *A46B 15/00* | (2006.01) |
| *A61C 17/26* | (2006.01) |
| *A61C 17/22* | (2006.01) |
| *A61C 17/24* | (2006.01) |
| *A46B 13/00* | (2006.01) |
| *A46B 13/02* | (2006.01) |
| *A46B 5/06* | (2006.01) |
| *A46B 7/06* | (2006.01) |
| *B08B 1/00* | (2006.01) |

(52) U.S. Cl.
CPC ......... *A61C 17/3418* (2013.01); *A46B 15/0081* (2013.01); *A46B 2200/1066* (2013.01); *A61C 17/26* (2013.01); *A61C 17/22* (2013.01); *A61C 17/24* (2013.01); *A46B 13/00* (2013.01); *A46B 13/02* (2013.01); *A46B 5/06* (2013.01); *A46B 7/06* (2013.01); *B08B 1/00* (2013.01); *B08B 1/001* (2013.01); *B08B 1/002* (2013.01)
USPC .................................. 134/6; 15/22.1; 15/22.3

(58) Field of Classification Search
CPC ........ A61C 17/22; A61C 17/24; A61C 17/26; A46B 13/00; A46B 13/02; A46B 5/06; A46B 7/06; B08B 1/00; B08B 1/001; B08B 1/002
USPC ....................................... 134/6; 15/22.1, 22.3
See application file for complete search history.

(56) References Cited

U.S. PATENT DOCUMENTS

| | | | | |
|---|---|---|---|---|
| 4,320,774 | A * | 3/1982 | Rogers | 15/22.1 |
| 4,791,945 | A * | 12/1988 | Moriyama | 15/22.1 |
| 5,276,932 | A * | 1/1994 | Byrd | 15/28 |
| 2013/0298340 | A1* | 11/2013 | Suwanbutr | 15/23 |

* cited by examiner

*Primary Examiner* — Bibi Carrillo
(74) *Attorney, Agent, or Firm* — Michael J. Feigin, Esq.; Feigin & Associates, LLC (57) ABSTRACT

In an embodiment of the disclosed technology, a toothbrush head formed of a bristled tread is rotatable about at least one vertically disposed sprocket. The toothbrush head has an elongated neck with sprockets extending axially therefrom. Bristles are wrapped around either or both sprockets. The bristles may be on a single belt wrapped around both sprockets. Alternatively, the bristles may extend from two spindles, each fitted around a sprocket. The sprockets rotate circumferentially within an upper head portion of the device. The bristles spin 360 degrees (full rotation) around the sprockets and within the stationary head. The head portion itself is replaceable or changeable, such that a handle portion may be used by multiple users or replaced.

12 Claims, 6 Drawing Sheets

FLAT BELT TREADMILL-LIKE ROTATION TOOTHBRUSH

FIELD OF THE DISCLOSED TECHNOLOGY

The disclosed technology relates generally to toothbrushes and, more specifically, to belt driven treadmill-like rotation bristled brushes.

BACKGROUND OF THE DISCLOSED TECHNOLOGY

Tooth brushing should be an integral part of everyone's daily hygiene routine. Poor dental hygiene can lead to future problems and expensive dentist bills. Therefore, maintenance of healthy teeth if of great importance. Many types of toothbrushes are available for brushing teeth.

Mechanical toothbrushes and toothbrush heads are known in the art. Various mechanisms have been employed for the purpose of cleansing teeth to the highest possible degree with the least amount of effort. Rotating and vibrating brush heads are set in motion by electric power, in order to cover a greater area and access to difficult to reach sections of the mouth and teeth. A problem with many existing mechanical toothbrushes is that they cause debris to be pushed towards the gums, instead of away from the gums.

Some analog and mechanical toothbrushes incorporate rubber bristles, in addition to standard bristles, for the purpose of massaging and cleaning the gums. However, many of these toothbrushes involve one set of bristles being in constant contact with segments of the teeth. As a result, these bristles become worn out, while other bristles, which incur less stress, such as those in the center, remain in good shape. Thus, there exists a need in the art for a mechanical toothbrush head with a replaceable rotating brush head that is cost-effective and easy to use.

SUMMARY OF THE DISCLOSED TECHNOLOGY

Therefore, it is an object of the disclosed technology to provide a flat belt, rotating toothbrush head having a replaceable bristle head rotating about a vertical axis.

As such, in an embodiment of the disclosed technology, a toothbrush has a housing with an upper head portion and a lower neck portion. Two spaced-apart drive sprockets extend through the upper head portion substantially parallel to the lower neck portion. A continuous, rotatable belt, with a tread on an interior side thereof, is simultaneously wrapped around each of the two spaced-apart drive sprockets. Each drive sprocket has a plurality of flanges extending out therefrom, such that at least one flange of each of the drive sprockets is constantly engaged with the tread when the tread is rotated by rotation of the two spaced-apart drive sprockets. The two spaced-apart drive sprockets are housed within the upper head portion of said housing. Bristles and/or rubber flanges extend from the belt.

In an embodiment, the drive sprocket is axially affixed to a spindle. The spindle extends through the lower neck portion and may be rotationally coupled to a drive mechanism. The drive mechanism may be, for example, an electric motor that is powered by batteries or an external electrical current.

The belt with bristles is enclosed in the upper head portion such that the bristles are partially exposed. A percentage of the bristles may be composed of rubber. The percentage of bristles that is composed of rubber may be between 25% and 75%. In an embodiment, the toothbrush may have a tongue scraper.

In a method of using the toothbrush described above, the continuous, rotatable belt is placed around each of the two spaced-apart drive sprockets. The method proceeds by causing at least one of the drive sprockets to rotate, wherein the rotation causes the belt to circumferentially rotate around the two drive sprockets. Next, the bristles of the belt are applied to a surface to be cleaned. In an additional step, the continuous, rotatable belt is removed from the two spaced-apart drive sprockets, and a new belt is then placed around each of the two spaced-apart drive sprockets. In order to install, remove and/or replace the belt, a top may be removed from the upper head portion prior thereto.

In another embodiment of the disclosed technology, a toothbrush head has two parallel sprockets extending axially from a distal end of an elongated neck. The two sprockets are disposed in a concave, upper portion of the toothbrush head. The toothbrush head further has two spindles with a plurality of bristles extending therefrom. The two spindles are disposed around the two sprockets. The toothbrush employs a drive shaft that is rotatably coupled to the two parallel sprockets. The drive shaft extends axially through the neck and terminates near a proximal end of the neck. In a method of use, the toothbrush rotates in such a manner as to push debris, plaque, and the like away from the gums as the direction of rotation of the belt is away from the gums and towards the center of the mouth (defined as a horizontal plane substantially (90%) equidistant between the roots of the top and bottom teeth).

In further embodiments of the toothbrush head, the end of the drive shaft closest to the proximal end of the neck is abutted by a drive mechanism that causes the drive shaft to rotate. The drive mechanism may be, for example, a battery-powered electric motor. In still a further embodiment, the toothbrush head may have a tongue scraper on the reverse side of the brush head.

DETAILED DESCRIPTION OF EMBODIMENTS OF THE DISCLOSED TECHNOLOGY

The disclosed technology is a toothbrush having a bristled belt that is wrapped around two drive sprockets. The drive sprockets rotate circumferentially within an upper head portion of the device. The bristles spin 360 degrees (full rotation) around the sprockets and within the stationary head. The head portion itself is replaceable or changeable, such that a handle portion may be used by multiple people, and/or when the head is worn out, may be replaced, while retaining the same handle. The handle, in embodiments, houses a gearbox and battery (or other power source) allowing one to power a motor in the handle portion, which passes the mechanical turning force through a spindle into the head region, rotating the bristles on the head, the bristles being on a tread.

Embodiments of the disclosed technology will become clearer in view of the following description of the drawings.

Figure 1:
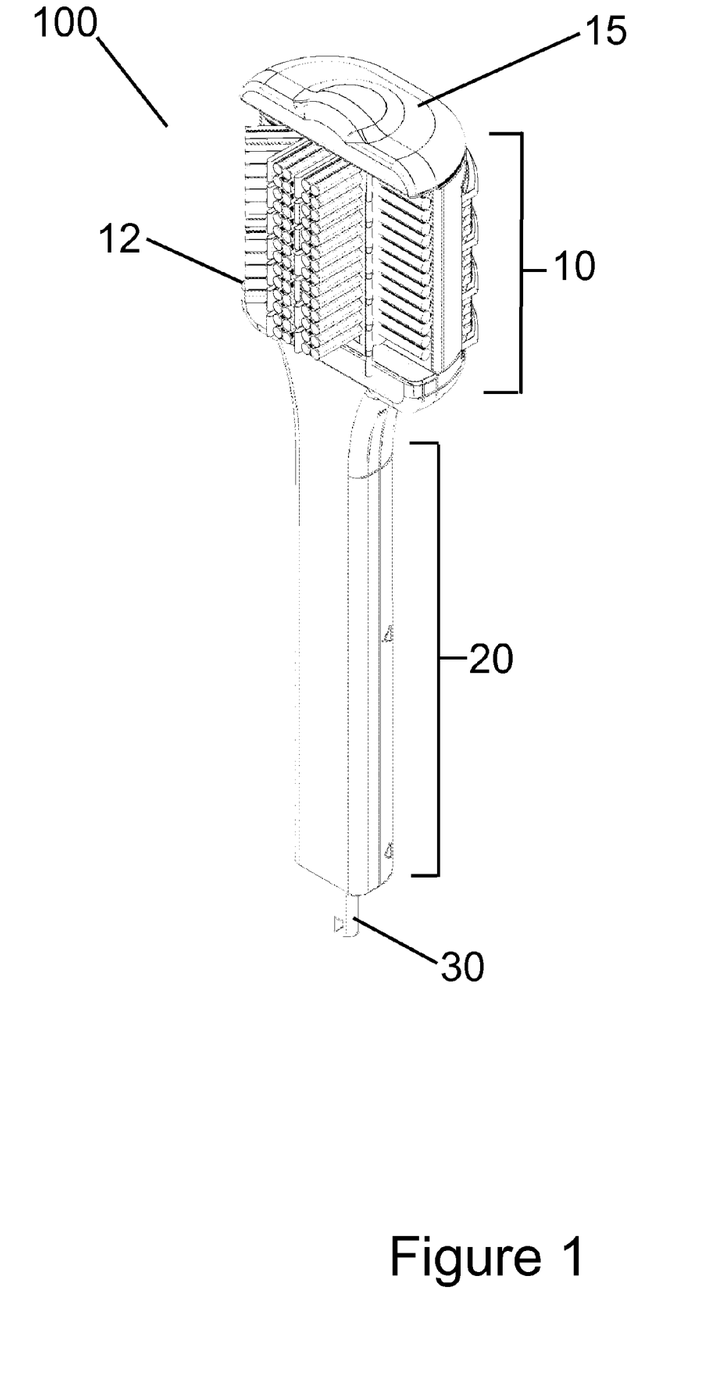
FIG. 1 shows a perspective view of a toothbrush head of an embodiment of the disclosed technology.

FIG. 1 shows a perspective view of a toothbrush head of an embodiment of the disclosed technology. The toothbrush head 100 is defined by a distal, upper head portion 10 and a proximal, lower neck portion 20, the head portion 10 extending from the neck portion 20. The head portion 10 has a top 15 and a concave, hollow front. A plurality of bristles 12 is disposed in the concave portion of the head portion 10. The bristles 12 are configured to rotate circumferentially within the head portion 10. Thus, in the embodiment shown, approximately half of the bristles are exposed at any given time, while the rest are enclosed within the head portion 10.

Figure 2:
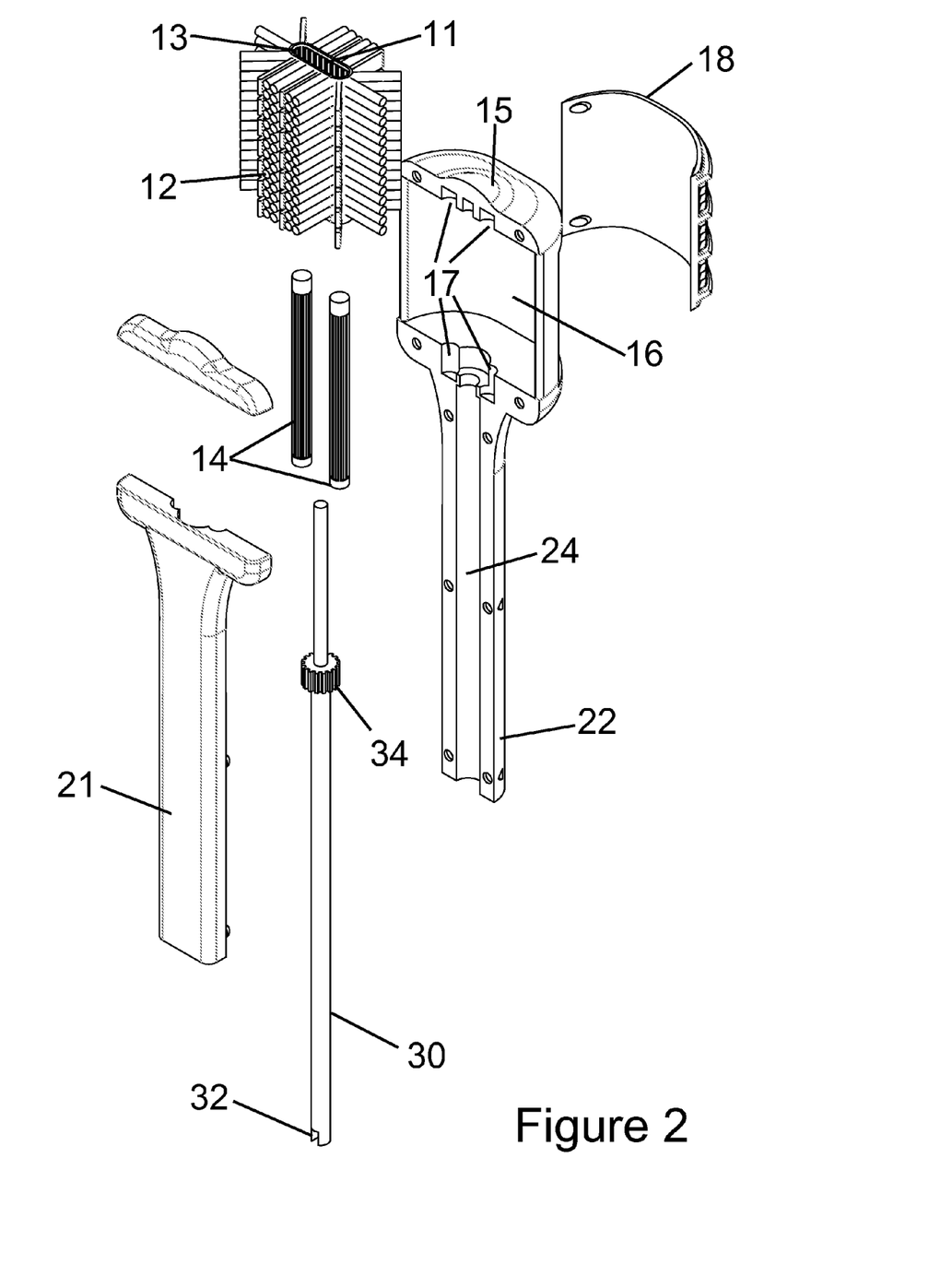
FIG. 2 shows a blown-apart view of a toothbrush head of an embodiment of the disclosed technology.

FIG. 2 shows a blown apart view of a toothbrush head of an embodiment of the disclosed technology. The plurality of bristles 12 extends from an exterior surface of a belt 13. The belt 13 may be flexible or semi-flexible, forming a continuous loop. An interior surface of the belt 13 may have treads 11. The belt 13 is adapted to be wrapped around two drive sprockets 14. The drive sprockets 14 are elongated spindles that extend axially from an upper end of the neck portion 20/a lower end of the head portion 10. The exterior surface of the drive sprockets 14 has flanges which correspond to the treads 11 of the belt 13. The belt 13 conforms to the circumference of the sprockets 14. The treads 11 are engaged with the flanges such that rotation of the sprockets 14 causes the belt 13, and in turn the bristles 12, to rotate circumferentially.

The sprockets 14 are fixed laterally within the upper portion 10 such that the sprockets are free to rotate. The ends of the sprockets 14 rest in corresponding slots 17 in the base of the upper portion 10 and the top 15 of the upper portion. The top 15 is removable, whereby the ends of the sprockets 14 and the top of the belt 13 are exposed. The sprockets 14 are arranged in parallel in the upper portion 10, extending through the front cavity 16 of the upper portion 10. A back plate 18 is disposed opposite to the front face on the back of the upper head portion 10. The back plate 18 may have a tongue scraper and/or gum massager disposed thereon.

The sprockets 14 (and in turn the bristles 12) may be caused to rotate by a drive shaft 30. The drive shaft 30 may have an axially fixed gear 34 that is coupled to the flanges of the sprockets 14. The drive shaft 30 may be an elongated member, extending from the base of the head portion 10 through a hollow cylindrical portal 24 in the lower neck portion 20. The drive shaft 30 may extend out of the base of the neck portion 20. The bottom end 32 of the drive shaft 30 may have a notch, slot, or other shape opening for engaging with drive mechanism (not shown). The neck portion 20 may generally be formed of a front member 21 and a back member 22, between which the drive shaft 30 may be disposed.

The drive mechanism may be, for example, an electric motor. The drive mechanism may be contained or inside a handle portion such that one or more toothbrush heads 100 may be interchangeably used on a single handle. One or more batteries may be enclosed within the handle of the toothbrush. The batteries may be conventional disposable batteries or rechargeable lithium ion batteries, or the like. The motor may be coupled to a gearbox which rotates to convert the mechanical force, by way of a gear, into rotation of the spindle extending into the upper region of the toothbrush.

The belt 13 forms a continuous loop sized to wrap around the sprockets 14. Bristles 12 are affixed to, and extend outwardly from, the belt 13. The bristles 12 may be formed of nylon, plastic, rubber, silicon or any combination thereof. In an embodiment, the bristles 12 are arranged in an alternating pattern, such that rows of bristles alternate between rubber and nylon. Alternatively, rubber flanges may account for every 4th row of bristles. Furthermore, different combinations of bristle lengths, hardnesses, and materials may be used.

Upon rotation of the sprockets 14, the bristles 12 are caused to rotate in a manner similar to a tank tread. The electric motor may be set to rotate at various speeds depending on a user's preference. The belt 13 may be formed of rubber or some other flexible material. The treads 11 may be molded from the rubber of the belt 13. The belt bristles 12 Will clean the upper and lower teeth at the same time. Thus, the rest of the toothbrush head 100 may be composed of plastic, metal or a similarly rigid or semi-rigid material. The toothbrush head 100 is disposable portion of the toothbrush as opposed to conventional mechanical toothbrush heads which have complicated mechanical heads that are costly to replace and will not clean the upper and lower teeth at the same time.

Referring still to FIG. 2, the lower neck portion 10 of the toothbrush may be formed of two opposing members 21 and 22 which enclose the drive shaft 30. The front member 21 and the back member 22 may be affixed to one another by way of fasteners or screws.

Figure 3:
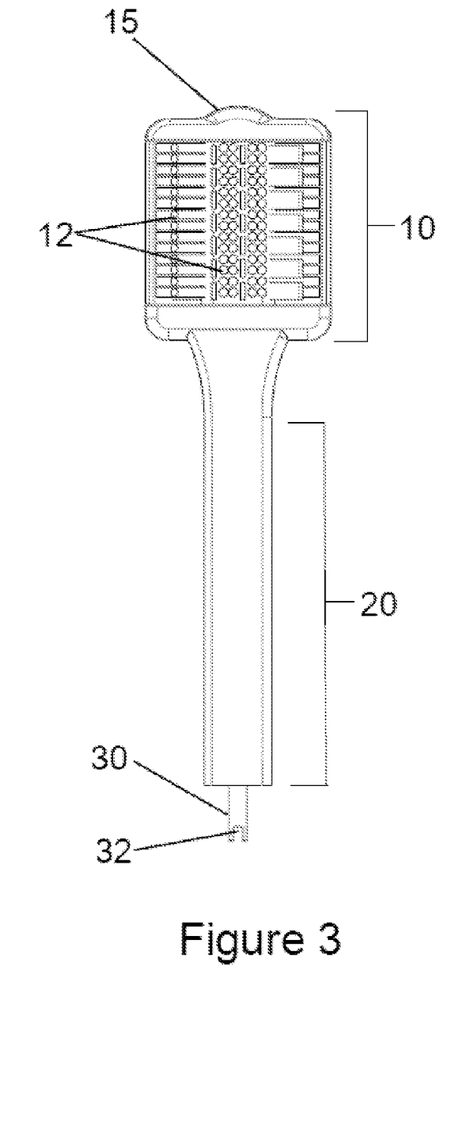
FIG. 3 shows a front elevation view of a toothbrush head of an embodiment of the disclosed technology.
Figure 4:
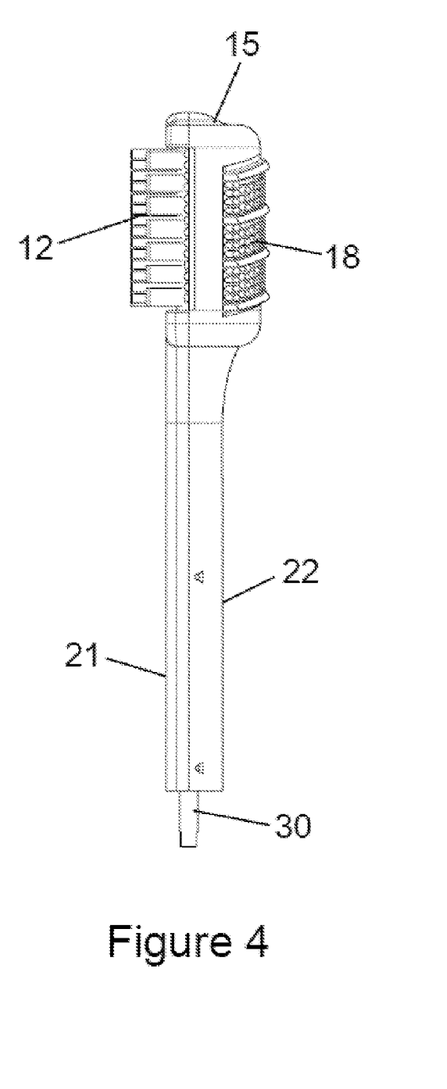
FIG. 4 shows a side elevation view of a toothbrush head of an embodiment of the disclosed technology.

FIG. 3 and FIG. 4 show a front and a side elevation view, respectively, of a toothbrush head of an embodiment of the disclosed technology. When used, the bristles 12 are inserted into the mouth and caused to rotate against the teeth. The longitudinal, rubber flanges are used to massage the gums and polish the teeth, while the thinner, softer, and closer together cluster of bristles are used to brush the teeth. As the belt 13 goes around the stationary portion of the head, there is alternation between rubber flanges and nylon bristles.

The rotation of the belt 13 also causes the orientation of the bristles 12 to change, thereby providing different cleaning angles against the teeth. For example, as a row of bristles 12 turns around one of the sprockets 14 and into the upper head portion 10, the angle of the bristles changes. As the angle changes, the orientation of the bristles with respect to the teeth changes, thereby reaching difficult portions between the teeth and cleans the upper and lower teeth at the same time.

In further embodiments of the disclosed technology, more or fewer sprockets 14 may be employed for driving the rotation of the belt. For example, a single sprocket may be directly affixed to the drive shaft, and a belt may fit snuggly on top of the sprocket. In another embodiment, three sprockets may be provided, one of which may be directly coupled or affixed to the drive shaft. The rotation of the single drive sprocket causes rotation of the belt and, in turn, the other two passive sprockets.

Figure 5:
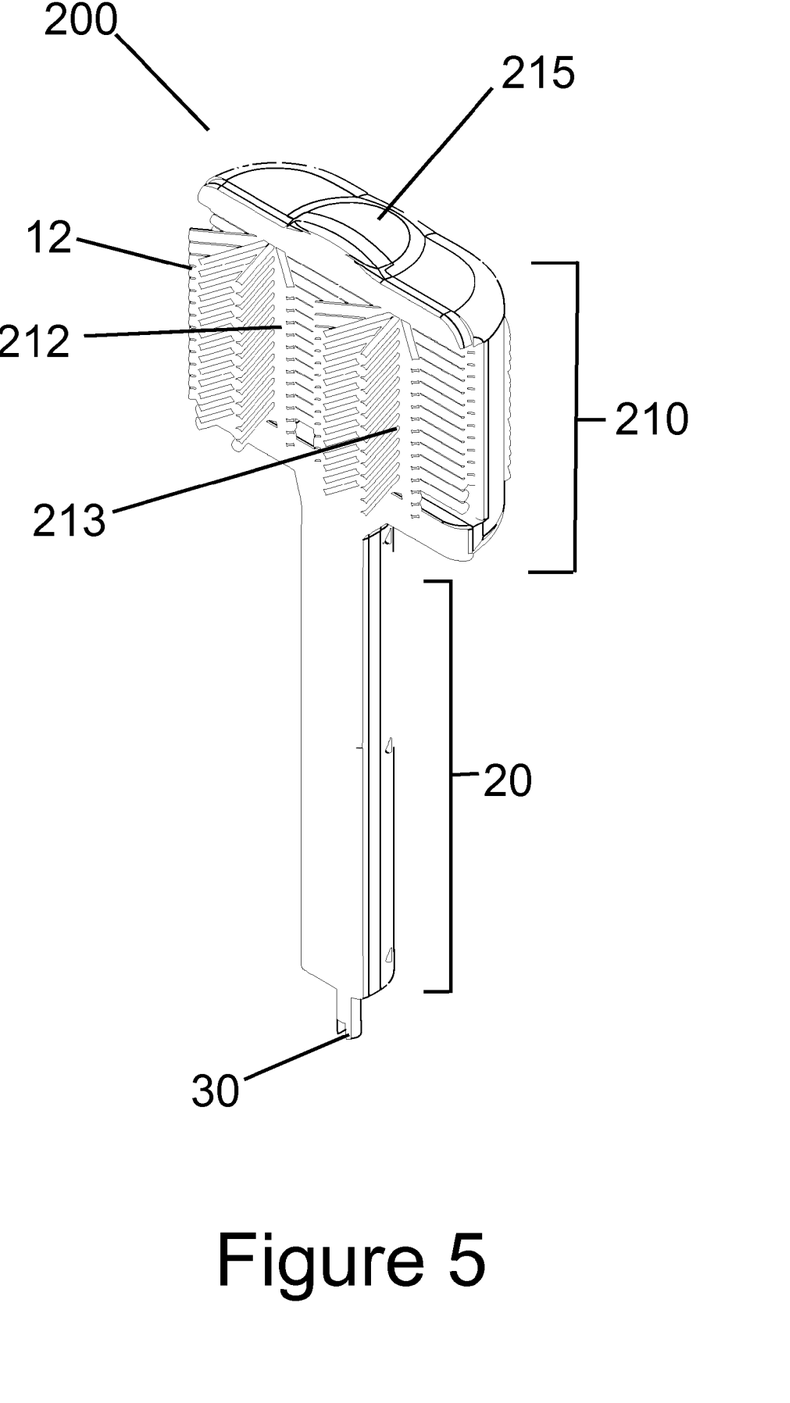
FIG. 5 shows a perspective view of another toothbrush head of an embodiment of the disclosed technology.

FIG. 5 shows a perspective view of another toothbrush head of an embodiment of the disclosed technology. The toothbrush head 200 is defined by a distal, upper head portion 210 and a proximal, lower neck portion 20. The head portion 210 extends from the neck portion 20. The head portion 210 has an integrated top 215 and a concave, hollow front 216. A plurality of bristles 12 is shown extending from the concave portion of the head portion 210. The bristles 12 are configured to rotate circumferentially within the head portion 210. Thus, in the embodiment shown, approximately half of the bristles are exposed at any given time, while the rest are enclosed within the head portion 210. A greater understanding of the interior mechanics of the toothbrush head 200 will be achieved with reference to FIG. 6.

Figure 6:
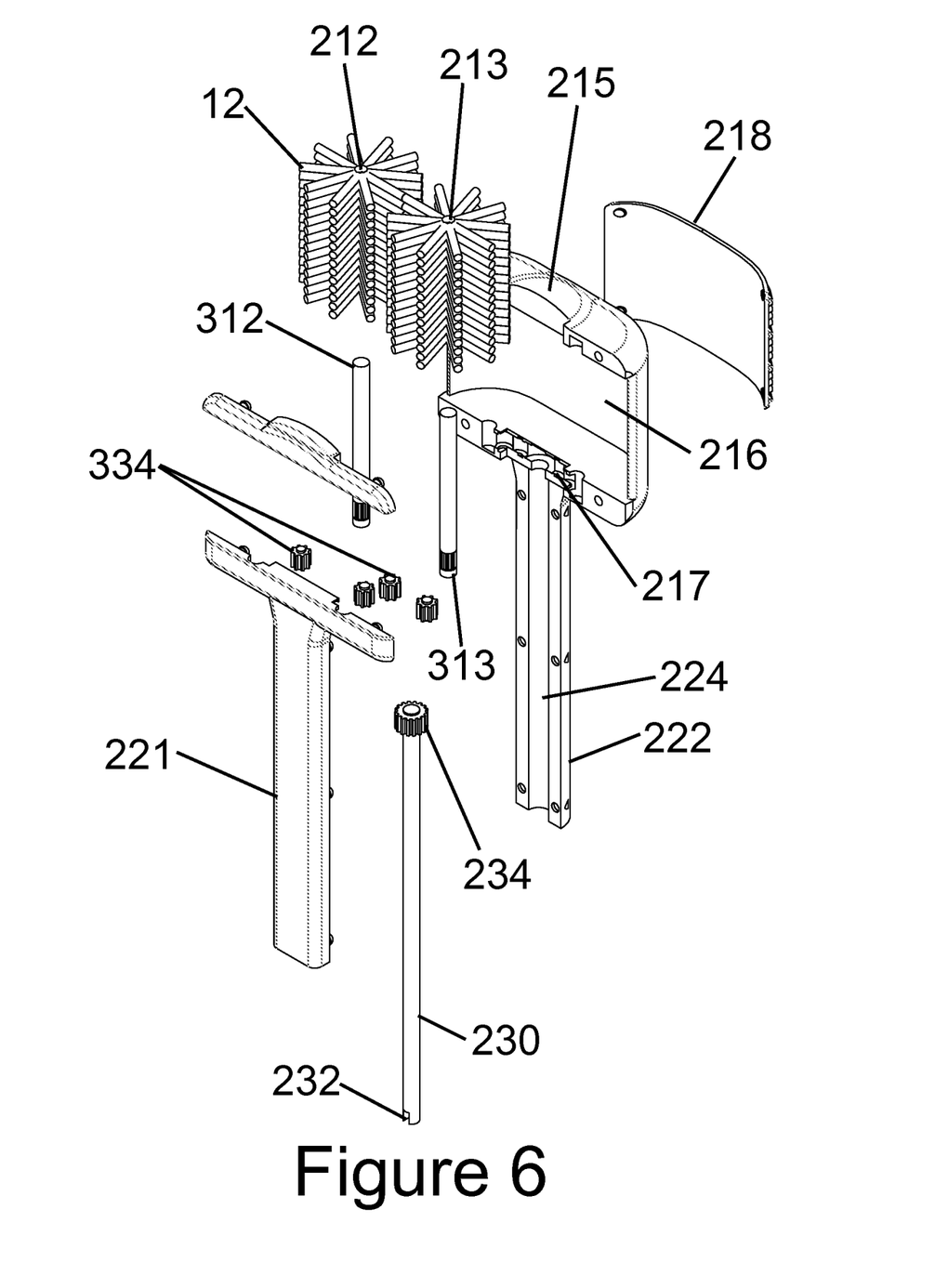
FIG. 6 shows a blown-apart view of another toothbrush head of an embodiment of the disclosed technology.

FIG. 6 shows a blown apart view of another toothbrush head of an embodiment of the disclosed technology. The plurality of bristles 12 extends from hollow spindles 212, 213. The hollow spindles 212, 213 are placed around drive sprockets 312, 313, respectively. The elongated drive sprockets 312, 313 extend axially from an upper end of the neck portion 20/a lower end of the head portion 210. A portion of the outer surface of the drive sprockets 312, 313 has flanges which are coupled to intermediary gears 334. The intermediary gears 334 are in turn coupled to an axial gear 234 affixed to a drive shaft 230.

The drive shaft 230 runs longitudinally through a hollow cylindrical portal 224 in the neck portion 20 of the toothbrush head 200. The drive shaft 230 extends from a lower end of the neck portion 20 and may protrude beyond the lower end as shown in FIGS. 5 and 6. A lower end of the drive shaft 230 may have a notch or slot 232 for coupling the drive shaft 230 to an electric motor or drive mechanism (not shown). The neck 220 may generally be formed of a front member 221 and a back member 222, between which the drive shaft 230 may be disposed.

The drive sprockets 312, 313 are fixed laterally within the upper portion 210 such that the sprockets are free to rotate. The ends of the sprockets 312, 313 rest in corresponding slots 217 in the base of the upper portion 210 and the top 215 of the upper portion. The top 215 is removable whereby the ends of the sprockets 312, 313 and the tops of the hollow spindles 212, 213 are exposed. The sprockets 312, 313 are arranged in parallel in the upper portion 210, extending through the front cavity 216 of the upper portion 210. A back plate 218 is disposed opposite to the front face on the back of the upper head portion 210. The back plate 218 may have a tongue scraper and/or gum massager disposed thereon.

The drive sprockets 312, 313 (and in turn the hollow spindles 212, 213) may be caused to rotate by a drive shaft 230 via the intermediary gears 334. The axially fixed gear 234 causes rotation of the intermediary gears 334 which, in turn, causes the sprockets 312, 313 to rotate.

The drive mechanism may be, for example, an electric motor. The drive mechanism may be disposed in a handle portion, such that one or more toothbrush heads 200 may be interchangeably used on a single handle. One or more batteries may be enclosed within the handle of the toothbrush. The batteries may be conventional disposable batteries or rechargeable lithium ion batteries or the like. The motor may be coupled to a gearbox which rotates to convert the mechanical force, by way of a gear, into rotation of the spindle extending into the upper region of the tooth brush.

Figure 7:
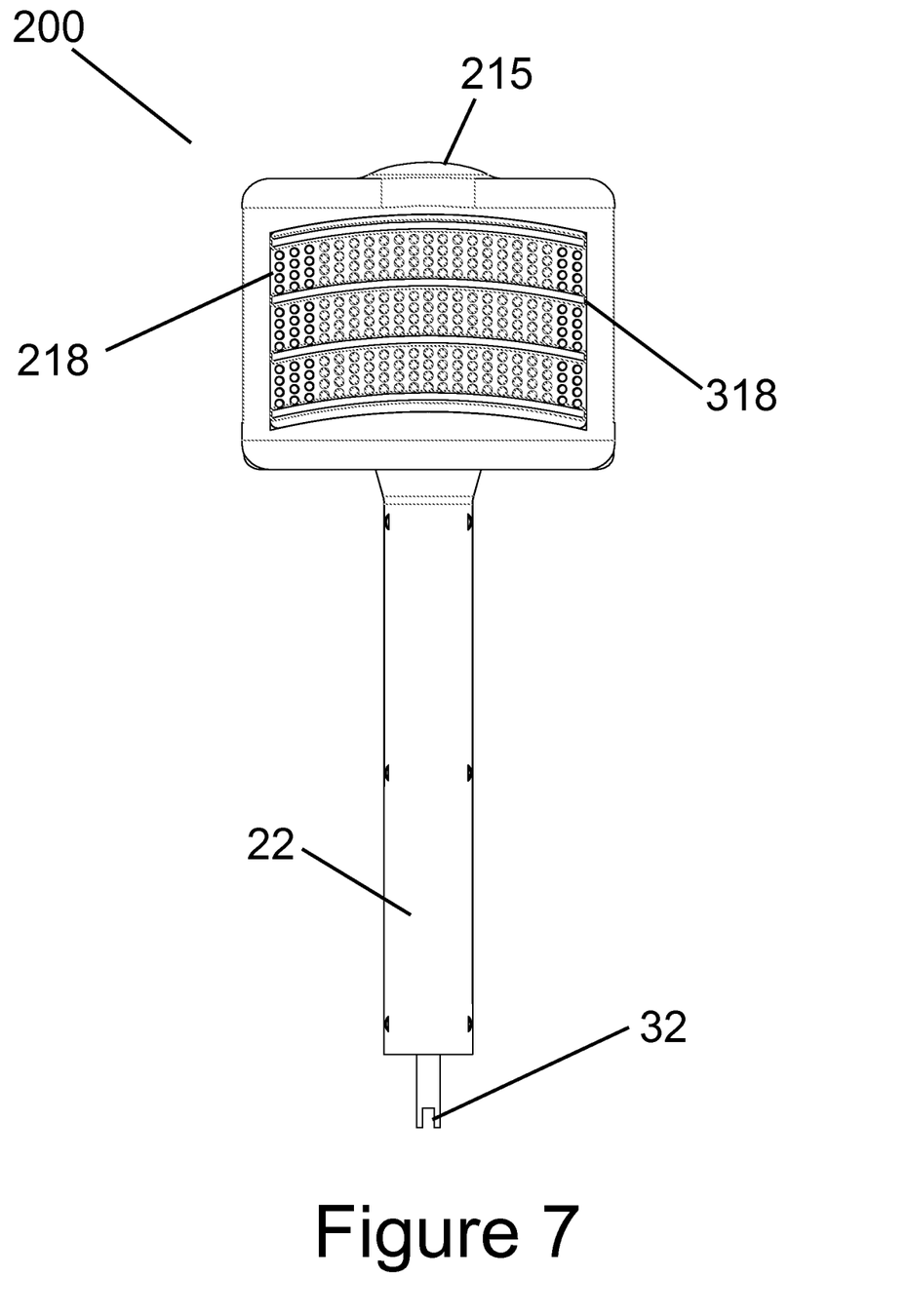
FIG. 7 shows a back elevation view of another toothbrush head of an embodiment of the disclosed technology.

FIG. 7 shows a back elevation view of another toothbrush head of an embodiment of the disclosed technology. The back 218 has one or more tongue cleaners/scrapers affixed thereto. Tongue scrapers are oral hygiene devices designed to clean the bacterial build-up, food debris, fungi, and dead cells from the surface of the tongue. The tongue scraper 318 may have multiple ribs which pull debris from the surface of the tongue when rubbed against.

In a method of use, one orients the brush such that the bristles rotate against the teeth and move upwards and/or (inclusive) downward in a direction away from the top and/or bottom (inclusive) gums. That is, any combination of brushing the top teeth or bottom teeth may take place in serial or simultaneously. The dirt, plaque, and surface of the teeth (inner or outer surface) is pushed against in a direction moving away from the gums in embodiments. That is, one brushes from the gums to the teeth, starting at the base of the teeth and moving away from the gums.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

I claim:

1. A method of using a toothbrush comprising the steps of: providing a toothbrush comprising:
a housing having an upper head portion and a lower neck portion;
two spaced-apart drive sprockets extending through said upper head portion substantially parallel to said lower neck portion; and
a continuous, rotatable belt with tread on an interior side thereof, simultaneously wrapped around each of said two spaced-apart drive sprockets, each of said drive sprockets having a plurality of flanges extending out therefrom, such that at least one flange of each of said drive sprockets is constantly engaged with said tread when said tread is rotated by rotation of said two spaced-apart drive sprockets, wherein said two spaced apart drive sprockets are housed within said upper head portion of said housing;
and a plurality of bristles extends outward from said belt;
placing said continuous, rotatable belt around each of said two spaced-apart drive sprockets; and
causing at least one of said drive sprockets to rotate, wherein said rotation causes said belt to rotate circumferentially around said two drive sprockets; and
applying said bristles of said belt to clean teeth and gums in the mouth.

2. The method of claim 1, wherein said drive sprocket is axially affixed to a spindle, said spindle extending through said lower neck portion.

3. The method of claim 1, wherein said tread is enclosed in said upper head portion, such that said tread is partially exposed.

4. The method of claim 1, wherein a percentage of said bristles is composed of rubber.

5. The method of claim 1, wherein the toothbrush further comprises a tongue scraper.

6. The method of claim 1, wherein said bristles rotate in a direction away from said gums and towards a horizontal center of the mouth.

7. The method of claim 1, wherein said applying is such that said bristles facing said teeth move in a direction from the gums towards a top of the teeth.

8. The method of claim 2, wherein said spindle is rotationally coupled to a drive mechanism.

9. The method of claim 4, wherein said percentage is between 25% and 75%.

10. The method of claim 8, wherein said drive mechanism is an electric motor.

11. The method of claim 10, wherein said electric motor is battery-powered.

12. A method of using a toothbrush comprising the steps of: providing a toothbrush comprising:
a housing having an upper head portion and a lower neck portion;
two spaced-apart drive sprockets extending through said upper head portion substantially parallel to said lower neck portion; and a continuous, rotatable belt with tread on an interior side thereof, simultaneously wrapped around each of said two spaced-apart drive sprockets, each of said drive sprockets having a plurality of flanges extending out therefrom, such that at least one flange of each said drive sprockets is constantly engaged with said tread when said tread is rotated by rotation of said two spaced-apart drive sprockets, wherein said two spaced apart drive sprockets are housed within said upper head portion of said housing; and a plurality of bristles extend outward from said belt; and placing bristles against at least one tooth and gums such that said placed bristles rotate in a direction from said gums to an exposed portion of said at least one tooth.

* * * * *